(12) United States Patent
Murai et al.

(10) Patent No.: US 7,641,642 B2
(45) Date of Patent: Jan. 5, 2010

(54) ABSORBENT ARTICLE

(75) Inventors: Atsushi Murai, Haga-gun (JP); Tetsuya Kusagawa, Haga-gun (JP); Miyuki Kondo, Haga-gun (JP); Mitsugu Hamajima, Haga-gun (JP)

(73) Assignee: Kao Corporation, Tokyo (JP)

( * ) Notice: Subject to any disclaimer, the term of this patent is extended or adjusted under 35 U.S.C. 154(b) by 19 days.

(21) Appl. No.: 10/322,667

(22) Filed: Dec. 19, 2002

(65) Prior Publication Data

US 2003/0144644 A1 Jul. 31, 2003

(30) Foreign Application Priority Data

Dec. 20, 2001 (JP) ............................. 2001-388202
Sep. 18, 2002 (JP) ............................. 2002-272241

(51) Int. Cl.
*A61F 13/15* (2006.01)
*A61F 13/20* (2006.01)

(52) U.S. Cl. ............................. 604/385.28; 604/385.24; 604/385.27; 604/385.29

(58) Field of Classification Search . 604/385.24–385.3, 604/387, 385.03
See application file for complete search history.

(56) References Cited

U.S. PATENT DOCUMENTS

| 5,746,732 A * | 5/1998 | Olsson et al. ........... 604/385.28 |
| 5,788,685 A | 8/1998 | Ronnberg et al. |
| 6,629,967 B1 * | 10/2003 | Simmons et al. ....... 604/385.27 |
| 6,706,029 B1 * | 3/2004 | Suzuki et al. .......... 604/385.28 |

FOREIGN PATENT DOCUMENTS

| EP | 0 678 290 A1 | 10/1995 |
| EP | 1208826 A2 | 5/2002 |
| EP | 1219274 A1 | 7/2002 |
| EP | 1232736 A1 | 8/2002 |
| GB | 2296445 A * | 7/1996 |
| GB | 2 329 842 A | 4/1999 |
| JP | 64-68503 A * | 3/1989 |

(Continued)

OTHER PUBLICATIONS

English translation of JP 2000-051268.*

(Continued)

*Primary Examiner*—Melanie J Hand
(74) *Attorney, Agent, or Firm*—Birch, Stewart, Kolasch & Birch, LLP

(57) ABSTRACT

An absorbent article 1 having a liquid retentive absorbent layer and a liquid impermeable leak preventive layer and including, in its longitudinal direction, an excretion portion facing section A which is placed opposite a wearer's liquid excretion portion, when in wear, and a rear section B which is placed more on the back side than the excretion portion facing section A, when in wear, wherein a leak preventive wall 5 is disposed on opposite side portions in the longitudinal direction, the leak preventive wall 5 having a basal wall portion and a planar elastic expansible/contractible portion connected to an upper end portion of the basal wall portion and being raised in the excretion portion facing section A and in the rear section B, and wherein a distance from an upper end portion of the basal wall portion to the leak preventive layer in the rear section is shorter than a comparable distance in the excretion portion facing section A.

5 Claims, 9 Drawing Sheets

FOREIGN PATENT DOCUMENTS

| | | |
|---|---|---|
| JP | 3-136654 A | 6/1991 |
| JP | 6-339497 A | 12/1994 |
| JP | 8-182702 | 7/1996 |
| JP | 8280735 | 10/1996 |
| JP | 2000-51268 A | 2/2000 |
| JP | 2000051268 A * | 2/2000 |
| JP | 2001-145667 | 5/2001 |
| WO | WO 96/07381 A2 | 3/1996 |
| WO | WO 97/41817 A1 | 11/1997 |
| WO | WO 9837842 A1 * | 9/1998 |
| WO | WO-01/05347 A1 | 1/2001 |
| WO | WO01/34084 A1 | 5/2001 |

OTHER PUBLICATIONS

Produktkatalog 1995-1996, Proctor & Gamble Hygien AB, Sweden.

* cited by examiner

ABSORBENT ARTICLE

CROSS-REFERENCE TO RELATED APPLICATION

This application claims the priority of Japanese Patent Application Nos. 2001-388202 filed Dec. 20, 2001 and 2002-272241 filed Sep. 18, 2002, which are incorporated herein by reference.

BACKGROUND OF THE INVENTION

This invention relates to an absorbent article such as a sanitary napkin, an incontinent pad and the like, and more particularly to an absorbent article which is excellent in fittablility and liquid leak preventive ability and in which those excellent properties are hardly degraded when worn.

An absorbent article has heretofore been known as an absorbent article such as a sanitary napkin, incontinent pad and the like, which is provided at a leak preventive wall with an elastic expansible/contractible portion which is longitudinally expanded and contracted and brought into planar contact with the wearer's skin.

Such a leak preventive wall is provided for the purposes of deforming an absorbent article into a three-dimensional shape (particularly, longitudinal concaved shape) for a favorably fit for the wearer and to enhance adhesibility to the wearer's skin, thereby surely preventing leakage of liquid.

However, the conventional absorbent article has such inconveniences that the leak preventive wall occasionally falls over or gets crushed when worn, thus making it unable to fully exhibit the expected function of the leak preventive wall of preventing leakage. This means that an excellent fit and liquid leak preventive ability can not be obtained in some instances.

Moreover, Japanese patent application Laid-Open No. 8-182702 discloses an absorbent article provided with a leak preventive wall having a leak preventive surface at an upper end portion thereof which is to be brought into planar contact with the wearer's skin. However, since the leak preventive wall is disposed only at the part opposite the wearer's liquid excretion portion, fittability in the rear section which is disposed more rearwards than the afore-mentioned part is not necessarily satisfactory in some instances.

Accordingly, an object of the present invention is to provide an absorbent article which is excellent in fittability and in liquid leak preventive ability and in which those excellent properties are hardly degraded when in wear.

SUMMARY OF THE INVENTION

The present invention has achieved the above object by providing an absorbent article comprising a liquid retentive absorbent layer and a liquid impermeable leak preventive layer and including, in its longitudinal direction, an excretion portion facing section which is placed opposite a wearer's liquid excretion portion, when in wear, and a rear section which is placed more on the back side than the excretion portion facing section, when in wear, wherein a leak preventive wall is disposed on opposite side portions in the longitudinal direction, the leak preventive wall comprising a basal wall portion and a planar elastic expansible/contractible portion connected to an upper end portion of the basal wall portion and being raised in the excretion portion facing section and in the rear section, and wherein a distance from an upper end portion of the basal wall portion to the leak preventive layer in the rear section is shorter than a comparable distance in the excretion portion facing section.

Also, the present invention has achieved the above object by providing a method for manufacturing an absorbent article comprising a liquid retentive absorbent layer, a liquid impermeable leak preventive layer and a leak preventive wall disposed along opposite side edges of the absorbent layer. In the present invention, the leak preventive wall comprises a basal wall portion and a planar elastic expansible/contractible portion connected to an upper end portion of the basal wall portion and being raised in an excretion portion facing section which is placed opposite a wearer's liquid excretion portion, when in wear, and a rear section which is placed more on the back side than the excretion portion facing section, when in wear, and a distance from an upper end portion of the basal wall portion to the leak preventive layer in the rear section is shorter than a comparable distance in the excretion portion facing section. The present invention also includes a method for manufacturing an absorbent article comprising a step of manufacturing a main body which comprises the absorbent layer or the absorbent layer and the leak preventive layer, a step of manufacturing an elastic expansible/contractible member which comprises a basal wall portion forming sheet portion having a constant width in the longitudinal direction and an elastic expansible/contractible portion connected to widthwise one end portion of the basal wall portion forming sheet portion, and a step of fixing the basal wall portion forming sheet portion of the elastic expansible/contractible member to opposite side portions of the main body so that a fixed position in the widthwise direction of the basal wall portion forming sheet portion in the excretion portion facing section and a fixed position in the widthwise direction of the basal wall portion forming sheet portion in the rear section are differentiated.

Also, the present invention has achieved the above object by providing a method for manufacturing an absorbent article comprising a liquid retentive absorbent layer, a liquid impermeable leak preventive layer and a leak preventive wall disposed along opposite side edges of the absorbent layer, the leak preventive wall comprising a basal wall portion and a planar elastic expansible/contractible portion connected to an upper end portion of the basal wall portion and being raised in an excretion portion facing section which is placed opposite a wearer's liquid excretion portion, when in wear, and a rear section which is placed more on the back side than the excretion portion facing section, when in wear, and a distance from an upper end portion of the basal wall portion to the leak preventive layer in the rear section is shorter than a comparable distance in the excretion portion facing section. The above object is also achieved by providing a method for manufacturing an absorbent article comprising a step of manufacturing a main body which comprises the absorbent layer or the absorbent layer and the leak preventive layer, a step of manufacturing an elastic expansible/contractible member which comprises a basal wall portion forming sheet portion having a constant width in the longitudinal direction and an elastic expansible/contractible portion connected to widthwise one end portion of the basal wall portion forming sheet portion, a step of fixing the elastic expansible/contractible member to opposite side portions of the main body at the other end portion of the basal wall portion forming sheet portion or in the nearby area thereof, a step of forming a multilayer portion having a predetermined length in the longitudinal direction of the elastic expansible/contractible member on that area of the basal wall portion forming sheet portion of the elastic expansible/contractible member which is disposed in the rear section, and a step of fixing longitudinal opposite end portions of the elastic expansible/contractible member onto the main body.

BRIEF DESCRIPTION OF THE DRAWINGS

The present invention will be more particularly described with reference to the accompanying drawings, in which:

FIG. 2(a) is a sectional view taken on line 2a-2a of FIG. 1 and FIG. 2(b) is a sectional view taken on line 2b-2b of FIG. 1;

FIG. 6(a) is a sectional view taken on line 6a-6a of FIG. 5 and FIG. 6(b) is a sectional view taken on line 6-b-6b of FIG. 5;

FIG. 9(a) is a sectional view taken on line 9a-9a of FIG. 8, FIG. 9(b) is a sectional view taken on line 9b-9b of FIG. 8. and FIG. 9(c) is a sectional view taken on line 9c-9c of FIG. 8;

FIG. 11(a) is a view showing a state in which a sanitary napkin is placed on a packaging material, FIG. 11(b) is a view showing a state in which the sanitary napkin is folded in the longitudinal direction together with the packaging material, and FIG. 11(c) is a view showing a state of completion of an item packaging of the sanitary napkin;

DETAILED DESCRIPTION OF THE PREFERRED EMBODIMENTS

The present invention will be described hereinafter based on its preferred embodiments.

Figure 1:
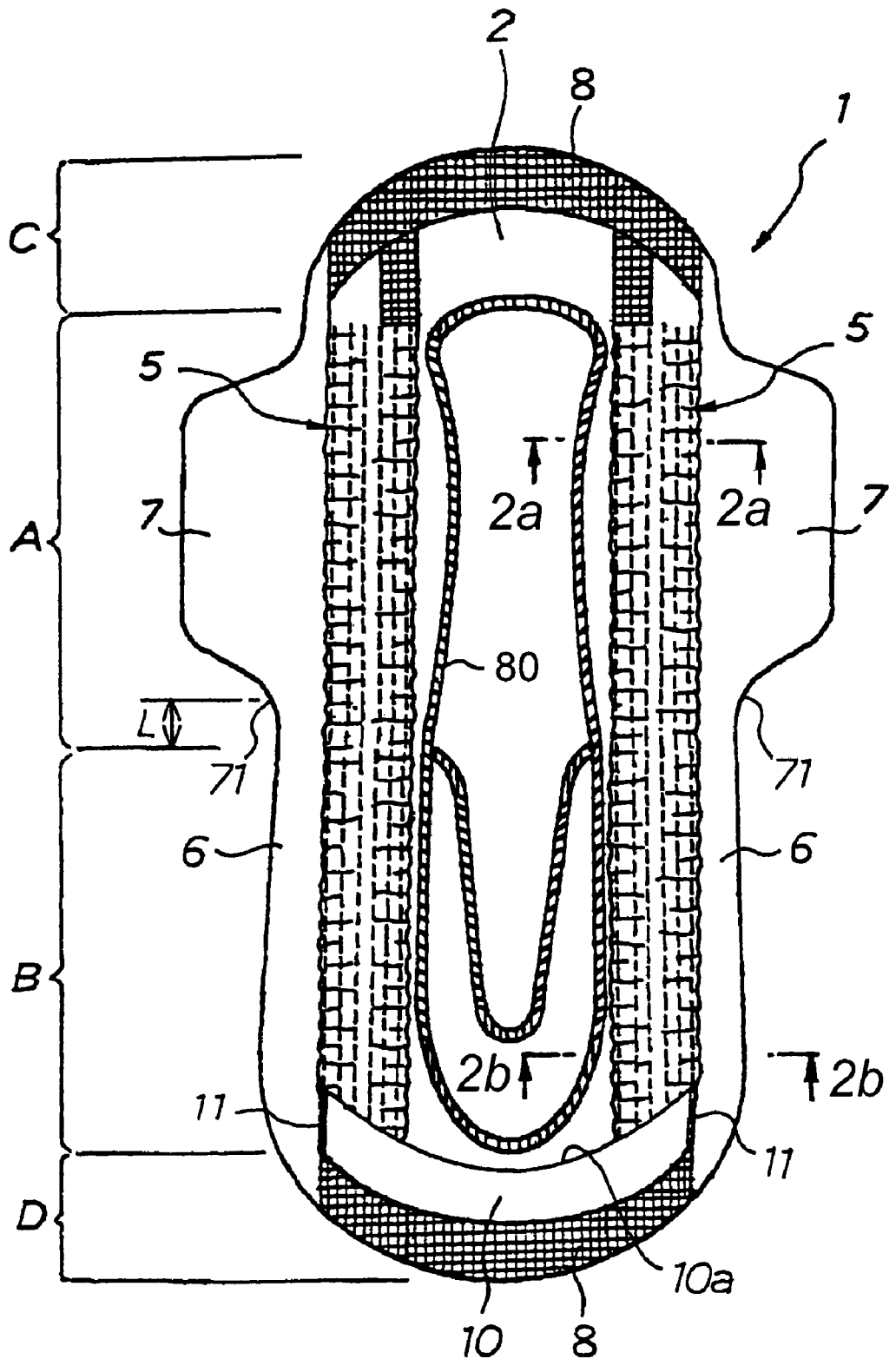
FIG. 1 is a plan view of a sanitary napkin according to a first embodiment of the present invention, when viewed from the topsheet side in its natural condition.
Figure 2A:
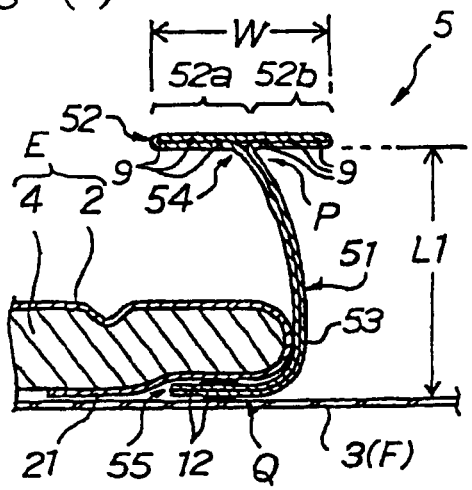
FIG. 2(a) and FIG. 2(b) are schematic views showing the sections of a leak preventive wall in the sanitary napkin of FIG. 1.
Figure 2B:
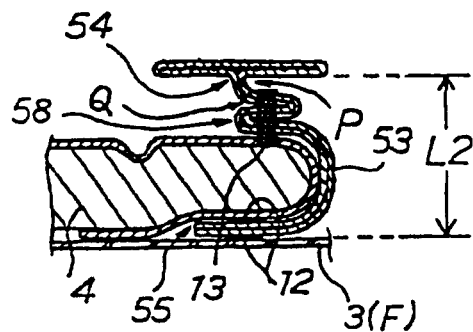
Figure 3:
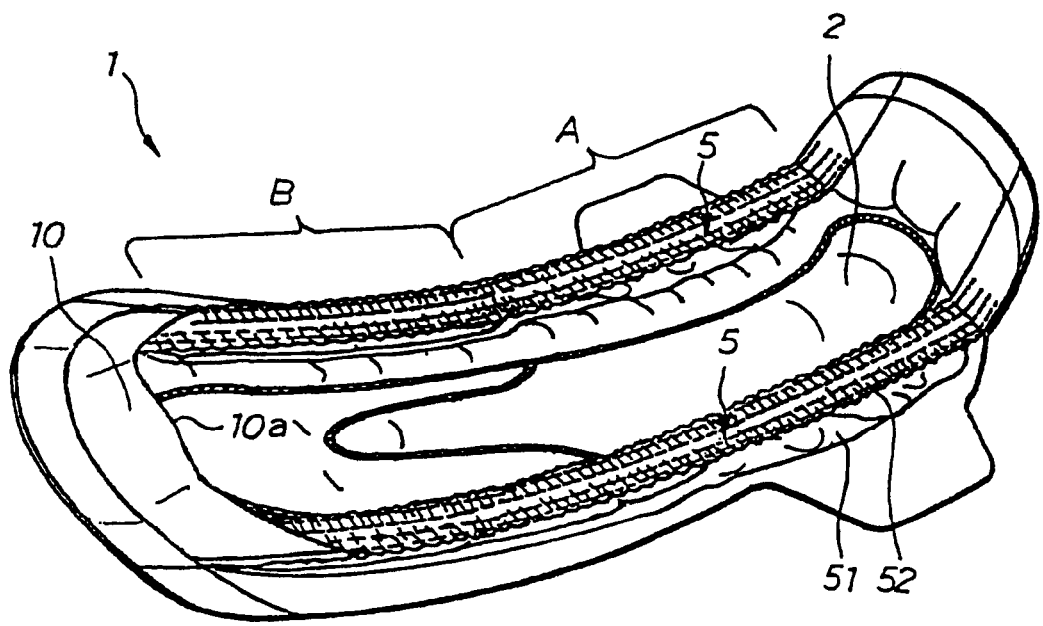
FIG. 3 is a perspective view showing a rough form of the sanitary napkin of FIG. 1, in its natural condition.

FIG. 1 shows a plan view of a sanitary napkin, when viewed from its topsheet side, according to a first embodiment of the present invention, FIGS. 2(a) and 2(b) schematically show the sections of a leak preventive wall at various parts of the sanitary napkin of FIG. 1, and FIG. 3 shows a perspective view of the sanitary napkin of FIG. 1.

As shown in FIGS. 1 through 3, a sanitary napkin 1 of this embodiment comprises a liquid retentive absorbent layer E and a liquid impermeable leak preventive layer F. The absorbent layer E comprises a liquid permeable topsheet 2 and a liquid retentive absorbent core 4, while the leak preventive layer F comprises a liquid impermeable backsheet 3. The absorbent core 4 is interposed between the topsheet 2 and the backsheet 3.

The topsheet 2 covers the entire area of the upper surface of the absorbent core is 4 and the side edges of the absorbent core 4 and is then wound towards the backsheet side. The backsheet 3 covers the lower surface of the absorbent core 4. The backsheet 3 extends outwards from each side edge of the absorbent core 4 to form a side flap 6. The side flap 6 further extends outwards at the location of an excretion portion facing section A, thereby forming a pair of wings 7. The topsheet 2 and the backsheet 3 extend, respectively, from front and rear ends of the absorbent core 4 and are joined together at the extended portions, thereby forming end seal portions 8. The absorbent core 4 and the topsheet 2 are integrally compacted to form a leak preventive groove 80 on the topsheet 2 side of the absorbent core 4.

The sanitary napkin 1 includes, in its longitudinal direction, the excretion portion facing section A which is placed opposite the wearer's liquid excretion portion when in wear, a rear section B which is placed more on the wearer's back side (rearward) than the excretion portion facing section A, when in wear, and a front end section C and a rear end section D which, respectively, form a front end section and a rear end section of the napkin 1. The boundary between the excretion portion facing section A and the rear section B in this embodiment is located at a generally central portion in the longitudinal direction of the napkin 1.

Each wing 7 in this embodiment is folded and fixed to the outer surface of an undergarment such as a shorts by a viscous agent or the like when in wear. The rear section B in the napkin 1 of the first and third embodiments, is a part which is away by 2 cm or more, preferably 3 cm or more from a wing basal end portion 71 (see FIG. 1) on the rear end side of the napkin 1. The distance between the rear section B and the wind basal portion 71 is indicated by L in FIG. 1.

The napkin 1 is provided at longitudinal opposite end portions thereof with a pair of leak preventive walls 5, 5 arranged along the longitudinal direction. The leak preventive wall 5 is arranged over the area located between the respective inner ends of the front and the rear end sections C, D of the napkin 1.

The leak preventive wall 5, as shown in FIG. 2, consists of a basal wall portion 51 raised from the vicinity of a side edge of the absorbent core 4, and a planar elastic expansible/contractible portion 52 connected to an upper end portion of the basal wall portion 51. The elastic expansible/contractible portion 52 is provided with an elastic member 9 which is disposed along the longitudinal direction of the napkin 1 and therefore, it has elastic expansibility/contractibility.

The leak preventive wall 5 is disposed along the longitudinal side edges of the absorbent layer E which comprises the topsheet 2 and the absorbent core 4. An upper surface (skin contact surface) of the elastic expansible/contractible portion 52 is generally in parallel with an upper surface (skin contact surface) of the absorbent layer E.

The elastic expansible/contractible portion 52 is planarly contacted with the wearer's skin at least in the excretion portion facing section A.

The elastic expansible and contractible portion 52 in connected to an upper end portion P of the basal wall portion 51 in the shape of T in section. That is, the elastic expansible/ contractible portion 52 comprises an inward extension 52a which extends inwardly in the direction P of the width of the napkin 1 from the upper end portion P of the basal wall portion 51 and an outward extension 52b which extends outwardly in the direction of the width of the napkin 1 from the upper end portion P. The two extensions 52a, 52b are generally same in extension width. Each of the extensions 52a, 52b is provided with three thread-like elastic members 9 which are spacedly arranged thereon. The elastic members 9 are disposed at least in the excretion portion facing section A and in the rear section B of the napkin 1.

The leak preventive wall 5 in the napkin 1 of this embodiment is raised in the excretion portion facing section A and in the rear section B, and is prevented from being raised (not raised) in the front end section C and in the rear end section D due to at least the fixture of the widthwise inner side of the elastic expansible/contractible portion 52 side (inward extension 52a) to the topsheet 2.

The elastic expansible/contractible portion 52 is fixed, at the outer parts of the longitudinal opposite ends of regions A and B where the leak preventive wall 5 is raised, and the widthwise inner side of the elastic expansible/contractible portion is not fixed to the topsheet 2 and the end seal portion 8. By contraction of the elastic expansible/contractible portion 52, the napkin 1 is, as shown in FIG. 3, concavely folded in its longitudinal overall configuration.

The leak preventive wall 5 in the napkin 1 of this embodiment is shorter in distance (straight line distance in a natural state, see FIG. 2(b)) L2 from the upper end portion P of the basal end portion 51 to the backsheet (leak preventive layer) 3 in the rear section B than the comparable distance (see FIG. 2(a)) L1 in the excretion portion facing section A.

According to the napkin of this embodiment, because the leak preventive wall 5 is raised in the excretion portion facing section A and in the rear section B, the following effects can be obtained.

(1) Even if the liquid excreted to the excretion portion facing section A flows rearwards, the liquid is prevented from leaking sideways by the leak preventive wall 5 in the rear section B.

(2) Also, even if the liquid excreted to the excretion portion facing section A flows sideways, it cannot climb over the leak preventive wall 5 and it flows towards the rear section and is absorbed in the adjacent absorbent core. Accordingly, leak can be prevented by effective utilization of absorbability of the absorbent core. The effect just mentioned is more significantly exhibited when the leak preventive wall 5 is continuously raised from the excretion portion facing section A to the rear section B.

Moreover, according to the napkin of this embodiment, because the distance L2 in the rear section B is shorter than the distance L1 in the excretion portion facing section A, the following effect can be obtained.

(3) Fittability (particularly, fittability to the wear's hip or nearby area of the hip) of the napkin 1 becomes good, and the napkin and the wearer's body are easily fit, thereby reducing the sense of incompatibility.

That is, the wearer's body line (curve) in the liquid excretion portion and the line more on the rear side (hip side) therefrom are not constant, and the curvature is smaller in the liquid excretion portion. In this embodiment, because the distance L2 in the rear section B is made shorter than the distance L1 in the excretion portion facing section A, the degree of curve (curvature) of the napkin in the rear section B and the degree of curve (curvature) of the napkin in the excretion portion facing section A can be made different easily and effectively, thereby enabling to make the overall configuration of the napkin more fittable to the curved configuration of the wearer's body.

If attempt is made, in order to increase the leak preventive ability, provide a leak preventive wall, which merely has the elastic expansibility/contractibility, also to the rear section, the degree of curve of the napkin is overly increased in the rear section, thereby degrading the fittability. For this reason, in the conventional absorbent article, no leak preventive wall is provided to the rear section. In this embodiment, however, by making different of the height of the leak preventive wall in the excretion portion facing section from that of the leak preventive wall in the rear section, both fittability and leak preventive ability can be made compatible.

Particularly, the leak preventive wall 5 of this embodiment has, in section, a T-like configuration including the inward extension 52a and the outward extension 52b, the following effect (4) can be obtained.

(4) Because of the upper end portion (elastic expansible/contractible portion 52) of the leak preventive wall, fittability to the wearer's body is enhanced and in addition, stability of the shape of the leak preventive wall becomes good, thus improving the above mentioned effect of leak prevention.

From a viewpoint of ensuring the above mentioned effects (1) through (3), the ratio (L1/L2) between the distance L1 from the upper end portion P of the basal end portion 51 to the backsheet (leak preventive layer) 3 in the excretion portion facing section A and the distance L2 from the upper end portion P of the basal wall portion 51 to the backsheet (leak preventive layer) 3 in the rear section B is preferably 1.2 to 6.0 and particularly preferably 1.5 to 3.0.

Moreover, from a viewpoint of leak prevention in the nearby area of the liquid excretion portion, the distance L1 is preferably 5 to 50 mm and particularly preferably 10 to 40 mm. Similarly, from a viewpoint of feel of use and leak prevention, the distance L2 is preferably 2 to 40 mm and particularly preferably 5 to 30 mm. Moreover, the width (distance between the distal end of the inward extension 52a and the distal end of the outward extension 52b) W (see FIG. 2(a)) of the elastic expansible/contractible portion 52 is preferably 6 to 40 mm and particularly preferably 10 to 30 mm from a viewpoint of fittability to the wearer's body and the effect of sideway leak prevention.

Figure 4:
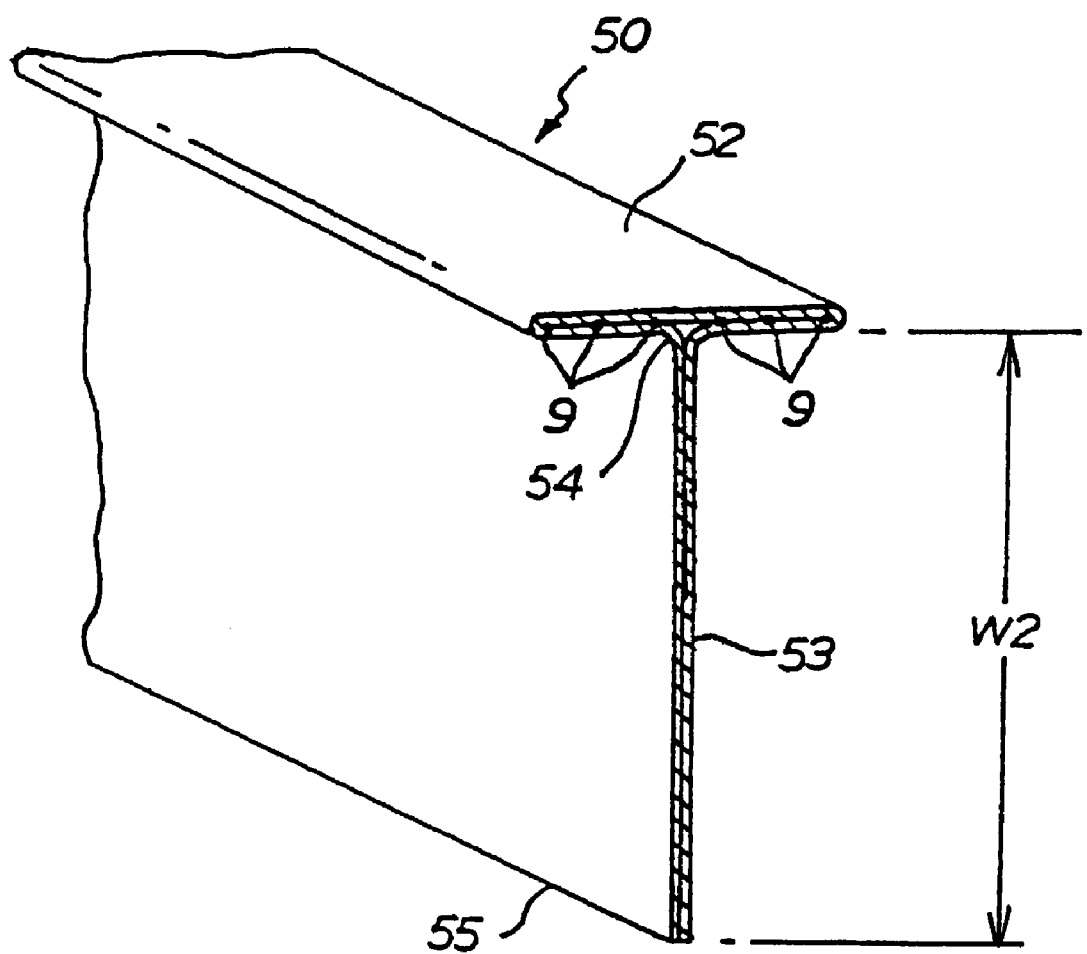
FIG. 4 is a perspective view showing an elastic expansible/contractible member for forming the leak preventive wall.

The leak preventive wall 5 of this embodiment is formed by fixing an elastic expansible/contractible member 50, which comprises, as shown in FIG. 4, a basal wall portion forming sheet portion 53 having a constant width W2 in the longitudinal direction and an elastic expansible/contractible portion 52 connected to widthwise one end portion 54 of the basal wall portion forming sheet portion 53 in the shape of T in section, to another component member (the topsheet 2, the backsheet 3 or the like) of the napkin 1.

It should be noted that the widthwise direction of the basal wall portion forming sheet portion refers to the widthwise direction of the basal wall portion forming sheet portion having a longitudinal direction and a width direction and that it is different from the widthwise direction of the napkin (absorbent article).

More specifically, in the excretion portion facing section A, the other end portion (end portion opposite to the end portion 54 located on the elastic expansible/contractible portion 52 side) of the basal wall portion forming sheet portion 53 of the elastic expansible/contractible member 50 is, as shown in FIG. 2(a), wound towards the lower surface side of the absorbent core 4, where it is fixed between the side portion 21 of the topsheet 2 and the backsheet 3 which is likewise wound towards the lower surface side of the absorbent core 4, by known joint means such as an adhesive agent 12 or the like.

The widthwise fixed position of the basal wall portion forming sheet portion 53 in the excretion portion facing section A is in the vicinity of the other end portion 55, and a lower end portion Q of the basal wall portion 51 in the excretion portion facing section A is formed at the position shown in FIG. 2(*a*).

In the rear section B, the basal portion forming sheet portion 53 of the elastic expansible/contractible member 50 is, as shown in FIG. 2(*b*), fixed to the upper surface side of the absorbent core 4 at a position near the one end portion 54 between the one end portion 54 and the other end portion 55, by known joint means such as heat sealing 13 or the like. The widthwise fixed position of the basal wall portion forming sheet portion 53 in the rear section B is the position near the one end portion 54 between the one end portion 54 and the other end portion 55 of the sheet portion 53, and the lower end portion Q of the basal wall portion 51 in the rear section B is formed at the position shown in FIG. 2(*b*).

Figure 6A:
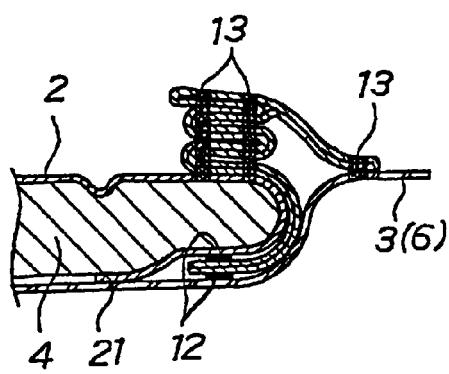
FIG. 6(a) and FIG. 6(b) are schematic views showing the sections of a leak preventive wall in the sanitary napkin of FIG. 5.
Figure 6B:
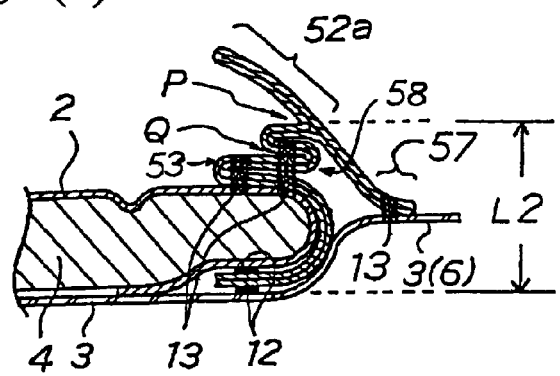

A multilayer portion 58 is formed on a portion of the basal wall portion forming sheet portion 53 in the rear section B. The multilayer 58 is the one which is provided at one portion of the basal wall portion forming sheet portion 53 and is a portion which is formed by folding a portion of the basal wall portion forming sheet portion 53 in such a manner as to become at least double and maintaining the folded state by joint means such as an adhesive agent, heat sealing or the like. However, the multilayer 58 does not include such a multilayer part in which, as shown in FIGS. 6(*a*) and 9(*c*), even the elastic expansible/contractible portion is fixed to the multilayer part formed by folding the basal wall portion forming sheet portion 53.

As shown in FIG. 2(*b*), the widthwise fixed position of the basal wall portion forming sheet portion 53 in case where the basal wall portion forming sheet portion 53 is fixed to another component member (topsheet, backsheet 3 or the like) at plural spots refers to the fixed position where the lower end portion Q of the basal wall portion 51 is produced, that is, the fixed position nearest to the end portion 54 on the elastic expansible contractible portion 52 side.

In this embodiment, from a viewpoint of manufacture, the leak preventive wall is formed using the elastic expansible/contractible member 50 which is even in width of the basal wall portion forming sheet portion 53 in the longitudinal direction, and by differentiating the fixed position of the sheet portion 53, the distance L2 from the upper end portion P of the basal wall portion to the leak preventive layer F in the rear section B is made shorter than the comparable distance L1 in the excretion portion facing section A.

As discussed in the foregoing, in this embodiment, since the distance L2 from the upper end portion P of the basal wall portion 51 to the backsheet (leak preventive layer) 3 in the rear section B is made shorter than the comparable distance L1 in the excretion portion facing section A by differentiating the widthwise fixed position of the basal wall forming sheet portion 53 in the excretion portion facing section A from the widthwise fixed position of the basal wall portion forming sheet portion 53 in the rear section B, thereby making the distance from the lower end portion Q to the upper end portion P of the basal wall portion 51 in the rear section B shorter than the comparable distance in the excretion portion facing section A, manufacture is easy compared with the case where the elastic expansible/contractible member is fixed in which the width of the basal wall portion forming sheet portion varies in the longitudinal direction. In addition, this constitution enables the formation of the distance L2 from the upper end portion P of the basal wall portion to the backsheet (leak preventive layer) 3 in the rear section C lower than the comparable distance L1 in the excretion portion facing section A.

In the napkin 1 of this embodiment, as shown in FIGS. 1 and 3, a leak preventive sheet 10 is disposed at the skin contact surface side of the rear end section D in the longitudinal direction of the napkin 1, and the leak preventive sheet 10 is fixed to the elastic expansible/contractible portion 52 of the raised leak preventive wall 5, so that an edge portion 10*a* of the leak preventive sheet 10 located on the longitudinal center side of the napkin 1 is spaced apart from the topsheet (absorbent layer) 2.

By disposing such a leak preventive sheet 10, a pocket-like space is formed at a rear part, and the pocket-like space can prevent the liquid, which has been flowed backwards, from leaking out. Since this pocket is fixed to the elastic expansible/contractible portion of the leak preventive wall, the pocket is spaced apart from the topsheet as the leak preventive wall is raised (at least the widthwise inner edge portion is spaced apart from the topsheet) and therefore, it is hardly crushed.

The leak preventive sheet 10 is, in the vicinity of the widthwise opposite end portions of the napkin, fixed to the place indicated by reference numeral 11 of FIG. 1 by known joint means (adhesive agent, heat sealing or the like) and, in the longitudinal direction of the napkin, integrally fixed to the end seal portions 8.

The napkin 1 of this embodiment can be manufactured, for example, through, among others, a step of manufacturing a main body which comprises an absorbent layer, a step of manufacturing the elastic expansible/contractible member 50 (see FIG. 4), a step of fixing the basal wall portion forming sheet portion 53 of the elastic expansible/contractible member 50 to opposite side portions of the main body so that, as shown in FIGS. 2(*a*) and 2(*b*), a fixed position in the widthwise direction of the basal wall portion forming sheet portion 53 in the excretion portion facing section A and a fixed position in the widthwise direction of the basal wall portion forming sheet portion 53 in the rear section B are differentiated, and a step for fixing longitudinal opposite end portions of the elastic expansible/contractible member 50 onto the main body, and a step of fixing the leak preventive layer F to the main body which comprises the absorbent layer E.

In the step of fixing the basal wall portion forming sheet portion 53 to the opposite side portions of the main body, after the end portion 55 or its nearby area of the basal end portion forming sheet portion is fixed to a part forming the excretion portion facing section A and the rear section B in the main body, other parts of the sheet portion 53 than the fixed end portion 55 or its nearby area may be fixed to the part forming the rear section B in the main body. It may also be fixed in the reverse order.

Moreover, although it can be formed in the step of fixing the basal wall portion forming sheet portion 53 to the main body, the multilayer portion 58 is preferably formed in the part which is disposed at the rear section B in the basal wall portion forming sheet portion 53, in the step of forming the elastic expansible/contractible member 50. It is also accepted that the main body, which comprises the absorbent layer E and the leak preventive layer (backsheet 3) F, is manufactured and then, the basal wall portion forming sheet portion 53 is fixed to the absorbent layer E and/or leak preventive layer F of the main body. In that case, the end portion 55 is fixed to the leak preventive layer F extended widthwise more outwards than the absorbent layer E, instead of being fixed to the lower part of the absorbent layer E as in FIG. 2.

Material for forming the sanitary napkin of this embodiment will now be described. As the topsheet 2, the absorbent core 4, the backsheet 3, the leak preventive sheet 10, and the sheet and the elastic member 9 of the elastic expansible/ contractible member 50 for forming the leak preventive wall 5, the material which is conventionally used for the absorbent article such as a sanitary napkin, an incontinent pad or the like can be used without any particular limitation. It should be noted that the backsheet may be a monolayer sheet or a laminated sheet, and that the laminated sheet may be a layered product of a liquid impermeable sheet and a liquid permeable sheet.

Instead of using the elastic member 9, the elastic expansible/contractible portion 52 may be composed of film or nonwoven fabric having expansible/contractible properties, laminated material of film having expansible/contractible properties and nonwoven fabric, material obtained by providing expansible/contractible properties to film having no expansible/contractible properties by applying uneven processing thereto. Also, the basal wall portion may have expansible/contractible properties as in the same with the elastic expansible/contractible portion. Although the leak preventive wall of this embodiment is formed of an elastic expansible/contractible material in which a basal wall portion forming sheet portion and an elastic expansible/contractible portion are integrally connected to each other, it is also accepted that the basal wall portion forming sheet portion and the elastic expansible/contractible portion are separately manufactured and then, the leak preventive wall is formed by using an elastic expansible/contractible material obtained by joining them.

Next, a sanitary napkin 1' according to a second embodiment of the present invention will be described with reference to FIGS. 5 through 7. With respect to the sanitary napkin 1' of the second embodiment, only those points different from the above-mentioned sanitary napkin 1 are described and description on the same points is omitted. With respect to those points, which are not particularly described, the description made with respect to the above-mentioned sanitary napkin 1 shall be applied, where appropriate.

Figure 5:
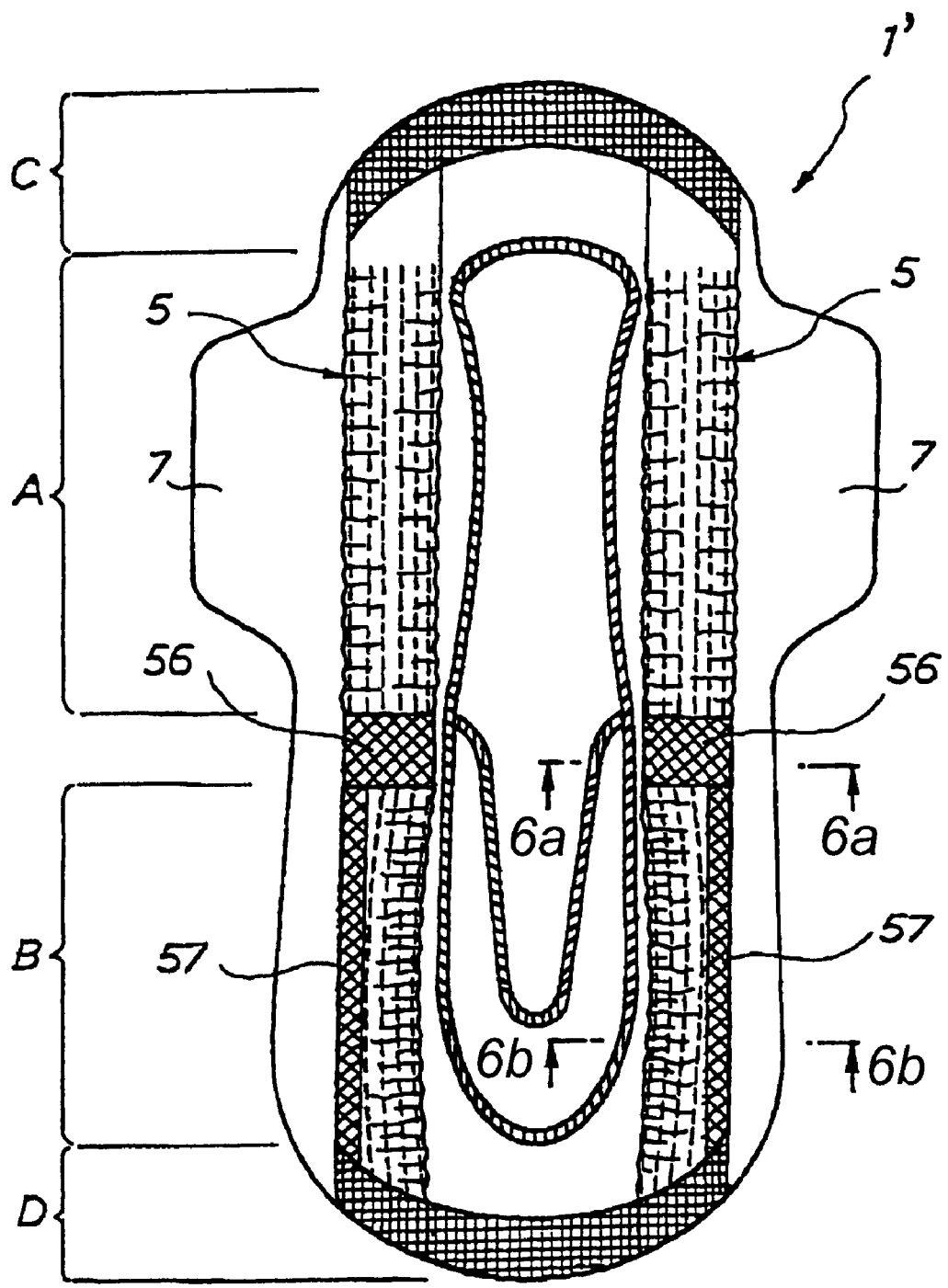
FIG. 5 is a plan view of a sanitary napkin according to a second embodiment of the present invention, when viewed from the topsheet side in its natural condition.
Figure 7:
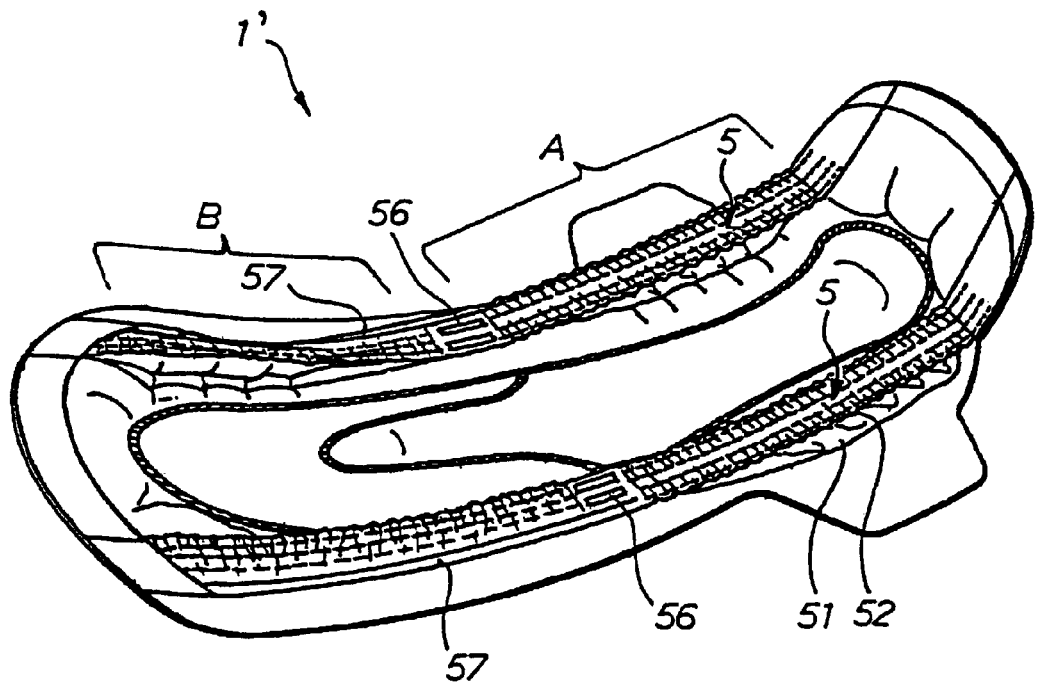
FIG. 7 is a perspective view showing a rough form of the sanitary napkin of FIG. 5, in its natural condition.

A leak preventive wall 5 in the sanitary napkin 1' of the second embodiment includes, as shown in FIGS. 5 and 7, a central fixed portion 56 where no leak preventive wall 5 is raised, between an excretion portion facing section A and a rear section B. In the central fixed portion 56, as shown in FIG. 6(*a*), since an elastic expansible/contractible portion 52 is prohibited from being raised (not raised) by being fixed over the widthwise entire area to a topsheet 2 or a backsheet 3 by known joint means such as heat sealing 13 or the like. Moreover, as shown in FIG. 6(*b*), a multilayer portion 58 is formed on a part of a basal wall portion forming sheet portion 53 in the rear section B.

It should be noted that the elastic expansible/contractible portion 52 in the central fixed portion 56 can be fixed to the topsheet 2 only at its widthwise inner side (inward extension 52*a*).

According to the sanitary napkin 1' of the second embodiment, the same function and effect can be exhibited as that of the first embodiment and in addition, it includes the central fixed portion 56. Accordingly, since the expanding/contracting stress of the elastic member in the region of the excretion portion facing section A is not transmitted to the region in the rear section B, more enhanced effect of the prevention of sideway leak and backward leak can be exhibited without being adversely affected by each other. That is, even if the elastic expansible/contractible portion in the excretion portion facing section A is subjected to stress due to walking action and opening/closing action of the legs, the stress is not transmitted to the rear section B owing to the presence of the central fixed portion 56. Accordingly, the leak preventive wall 5 in the rear section B can be kept in a stable condition irrespective of the action of the legs.

Moreover, in the sanitary napkin 1' of the second embodiment, as shown in FIG. 6(*b*), a side end portion 57 on the widthwise outer side of the elastic expansible/contractible portion 52 in the rear section B is fixed onto a backsheet 3 (side flap 6) which is extended more outwards than the side edge portion of an absorbent core 4.

Owing to the above feature, the widthwise inner side (inward extension 52*a*) of the elastic expansible/contractible portion 52 can surely be raised and therefore, a pocket formed between the elastic expansible/contractible portion 52 and the topsheet 2 is hardly crushed even if a wearing pressure is applied to the pocket when in wear. Moreover, since the outward extension 52*b* is bonded to the backsheet 33, oozing leak of liquid can be more reduced.

Figure 8:
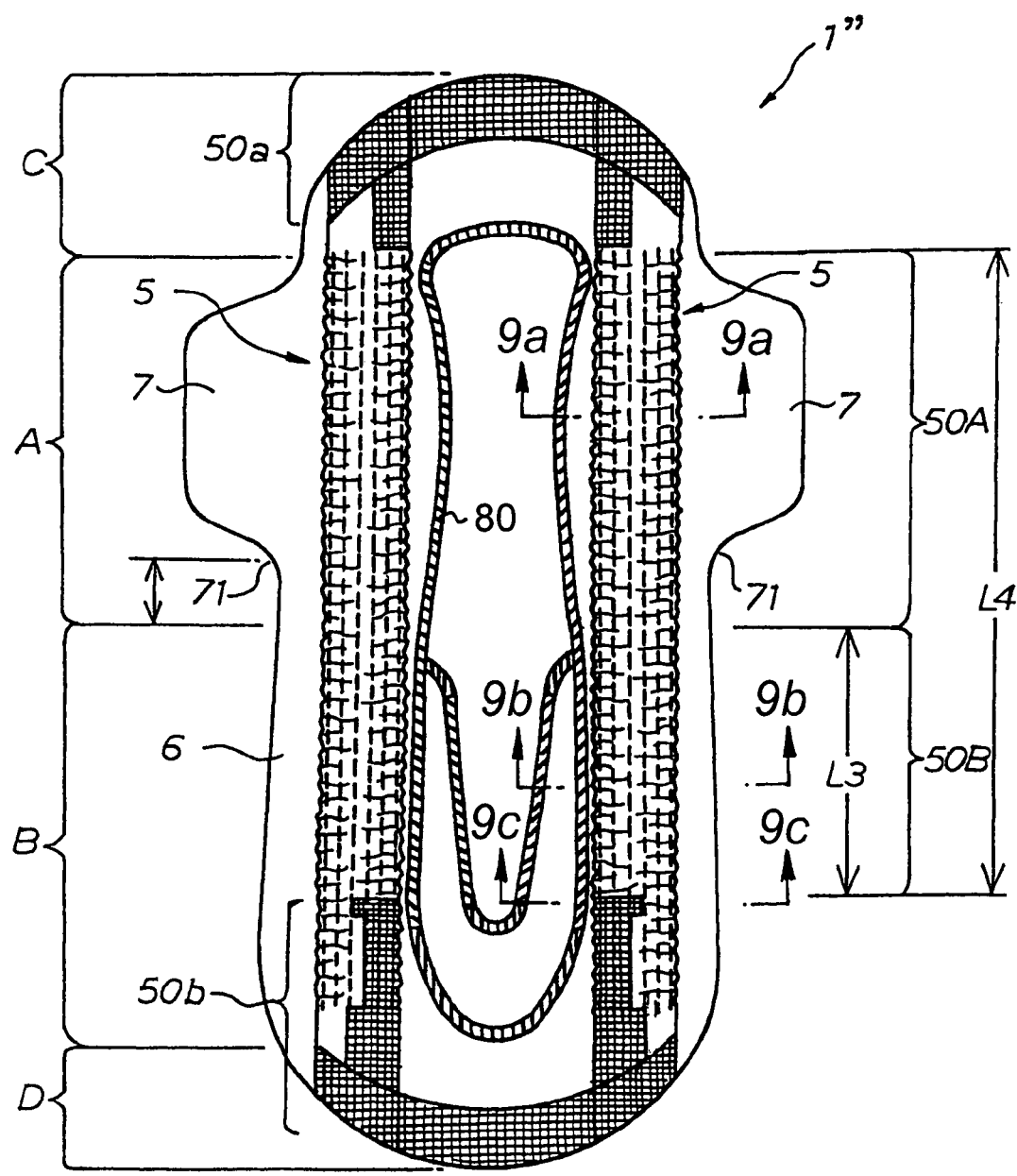
FIG. 8 is a plan view of a sanitary napkin according to a third embodiment of the present invention, when viewed from the topsheet side in its natural condition.

Next, a sanitary napkin 1" according to a third embodiment of the present invention will be described with reference to FIGS. 8 through 10.

With respect to the sanitary napkin 1" of the third embodiment, only those points different from the above-mentioned sanitary napkin 1 are described and description on the same points is omitted. With respect to those points, which are not particularly described, the description made with respect to the above-mentioned sanitary napkin 1 shall be applied, where appropriate.

A leak preventive wall 5 in this embodiment has an inward extension 52*a* and an outward extension 52*b* which is different in extension width from the portion 52*a*. The ratio (the former:the latter) of the extension width of the inward extension 52*a* and that of the outward extension 52*b* is about 3:2 to 5:1. A pair of leak preventive walls 5, 5 are formed along the longitudinal opposite side edges of an absorbent layer E comprising a topsheet 2 and an absorbent core 4.

Figure 9A:
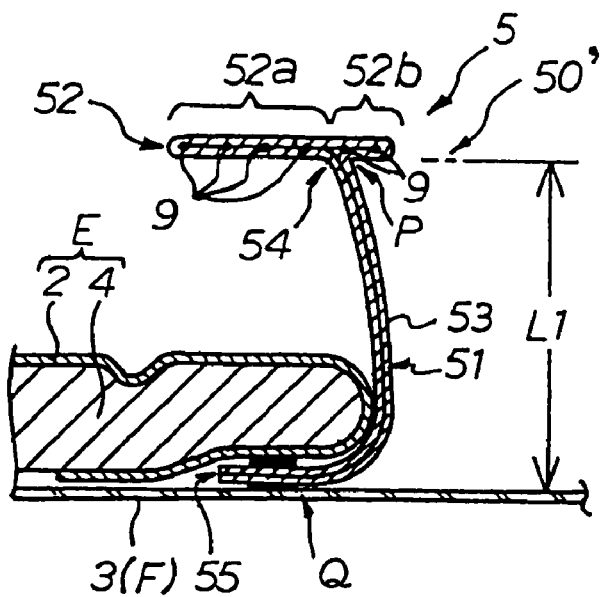
FIG. 9(a), FIG. 9(b) and FIG. 9(c) are schematic views showing the sections of a leak preventive wall in the sanitary napkin of FIG. 8.
Figure 9B:
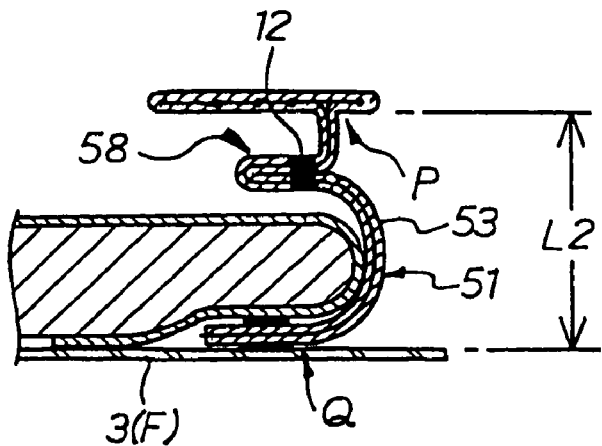
Figure 9C:
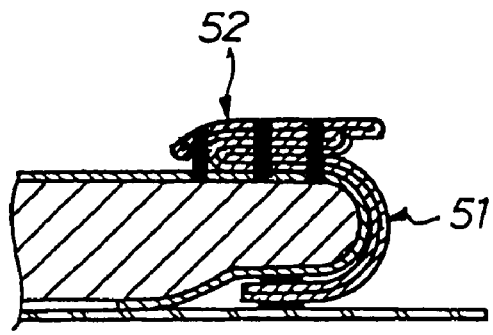
Figure 10:
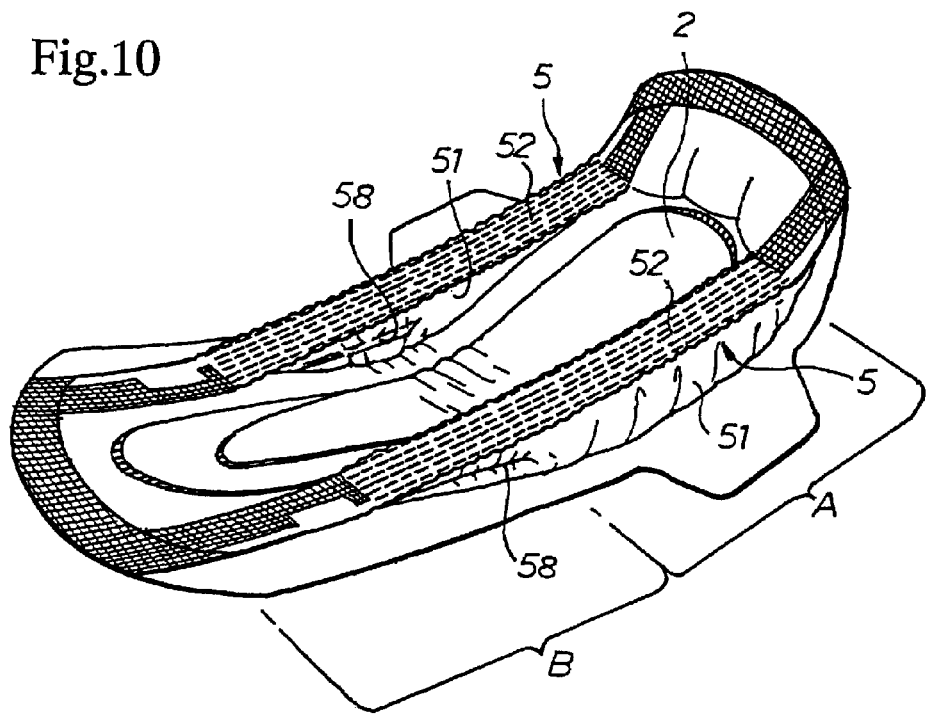
FIG. 10 is a perspective view showing a rough form of the sanitary napkin of FIG. 8, in its natural condition.

Each leak preventive wall 5 in this embodiment is formed by fixing an elastic expansible/contractible member 50' to another component member (the topsheet 2, the backsheet 3 or the like) of the napkin 1", as shown in FIGS. 9(*a*) through 9(*c*). The elastic expansible/contractible member 50' has the same construction as the above-mentioned elastic expansible/contractible member 50 only excepting the connecting place of a basal wall portion forming sheet portion 53 with respect to an elastic expansible/contractible portion 52.

A basal wall portion forming sheet portion 53 of the elastic expansible/contractible member 50' is fixed at the nearby area of an end portion 55 opposite to the end portion 54 on the elastic expansible/contractible portion 52 side between a side portion 21 of the topsheet 2 and the backsheet 3 by known joining means such as an adhesive agent 12 or the like, as shown in FIGS. 9(*a*) through 9(*c*), at the lower surface side of the absorbent core 4 over a front end section C and a rear end section D of the napkin 1". In the front end section C and the rear end section D, at least the widthwise inner side (inward extension 52*a*) of the elastic expansible/contractible portion 52 is fixed to the topsheet 2.

By providing a multilayer portion 58, as shown in FIG. 9(*b*), to a part of a basal wall portion 51 of the elastic expansible/contractible member 50' which is disposed in a rear section B, the leak preventive wall 5 of this embodiment makes the distance L2 (see FIG. 9(*b*)) from an upper end portion P of the basal wall portion 51 to the backsheet 3 (leak preventive layer F) shorter than a comparable distance L1 (see FIG. 9(*a*)) in an excretion portion facing section A.

That is, in the third embodiment, from a viewpoint of manufacture, the leak preventive wall is formed using the elastic expansible/contractible member 50' which is even in width of the basal wall portion forming sheet portion 53 in the longitudinal direction, and by providing the multilayer portion 58 to the basal wall portion forming sheet portion 53 in the rear section B, the distance L2 from the upper end portion P of the basal wall portion to the leak preventive layer F in the rear section B is made shorter than the comparable distance L1 in the excretion portion facing section A.

It should be noted that the multilayer portion 58 is formed by folding a widthwise part of the basal wall portion forming sheet portion 53 such that the faces on the same side of the sheet portion are faced with each other, and then, by joining the mutually facing surfaces by known joint means such as an adhesive agent, heat sealing or the like.

The multilayer portion 58 is formed over a predetermined length in the longitudinal direction of the elastic expansible/contractible member 51'. In the longitudinal direction of the napkin 1", the length L3 of the part where the multilayer portion 58 is formed, is preferably 15 to 45% and particularly preferably 20 to 30% of the overall length L4 (see FIG. 8) of the part where the leak preventive wall 5 is raised.

The napkin 1" of this embodiment can more efficiently be manufactured by a method for manufacturing an absorbent article comprising, for example a step of manufacturing a main body which comprises the absorbent layer E or the absorbent layer E and the leak preventive layer F, a step of manufacturing an elastic expansible/contractible member 50' which comprises a basal wall portion forming sheet portion 53 having a constant width in the longitudinal direction and an elastic expansible/contractible portion 52 connected to widthwise one end portion of the basal wall portion forming sheet portion 53, a step of fixing the elastic expansible/contractible member 50' to opposite side portions of the main body at the other end portion 55 of the basal wall portion forming sheet portion 53 or in the nearby area thereof, a step of forming a multilayer portion 68 having a predetermined length in the longitudinal direction of the elastic expansible/contractible member 50' on that area of the basal wall portion forming sheet portion 53 of the elastic expansible/contractible member 50' which is disposed in the rear section B, and a step of fixing longitudinal opposite end portions of the elastic expansible/contractible member 50' onto the main body.

In a preferred method for manufacturing the napkin 1" of this embodiment, the step of manufacturing a main body comprising an absorbent layer E by integrating a topsheet 4 with an absorbent core 4 and the step of manufacturing an elastic expansible/contractible member 50' comprising a basal wall portion forming sheet portion 53 having a constant width in the longitudinal direction and an elastic expansible/contractible portion 52 connected to widthwise one end portion of the sheet portion 53, are conducted in an optional order (including conducting simultaneously). In the step of manufacturing the elastic expansible/contractible member 50', a multilayer portion 58 is formed on that part of the basal wall portion forming sheet which is disposed in the rear section B, over a predetermined length in the longitudinal direction of the elastic expansible/contractible member 50'.

Then, as shown in FIGS. 9(*a*) through 9(*c*), a step of fixing the elastic expansible/contractible member 50' to the opposite side portions of the absorbent layer (main body) at the other end portion 55 of the basal wall portion forming sheet portion 53 or its nearby area, a step of integrating the main body comprising the absorbent layer E with the leak preventive layer (backsheet 3) F, and a step of fixing the longitudinal opposite end portions 50*a*, 50*b* of the elastic expansible/contractible member 50' onto the absorbent layer (main body) E, are executed in this order.

In the sanitary napkin 1" thus obtained, both the part 50A having no multilayer portion 58 formed thereon and the part 50B having multilayer portion 58 formed thereon are formed between the opposite end portions 50*a*, 50*b* of the elastic expansible/contractible members 50'.

Instead of manufacturing the main body comprising the absorbent layer E and then fixing the other end portion 55 of the basal wall portion forming sheet portion 53 to the opposite side portions of the absorbent layer E as in the above-mentioned manufacturing method, it is also accepted that the main body comprising the absorbent layer E and the leak preventive layer (backsheet 3) F is manufactured and then, the other end portion 55, or its nearby area, of the basal wall portion forming sheet portion 53 to the absorbent layer E and/or the leak preventive layer F of the main body. It is also accepted that the multilayer portion 58 is formed on the elastic expansible/contractible member 50' before it is fixed to the main body comprising the absorbent layer E, or the absorbent layer E and the leak preventive layer F. It is also an interesting alternative that the multilayer portion 58 is formed on the elastic expansible/contractible layer after it is fixed to the opposite side portions of the main body.

The napkin 1" of this embodiment is preferably individually packaged and commercially sold, distributed and so on. An individually packaged item (item packaging) of the sanitary napkin 1" can be obtained, for example, as follows.

Figure 11A:
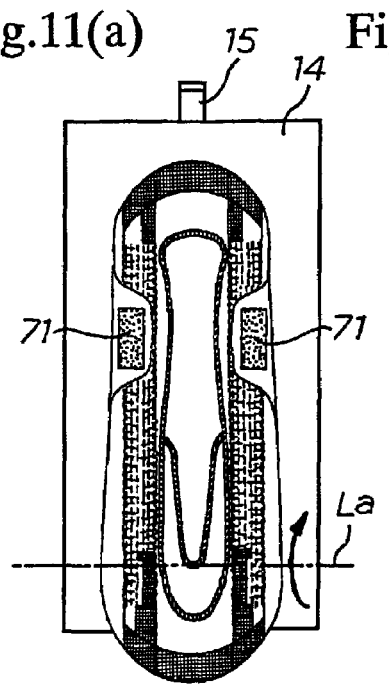
FIG. 11(a), FIG. 11(b) and FIG. 11(c) are schematic views showing the manufacturing process of an item packaging of a sanitary napkin.
Figure 11B:
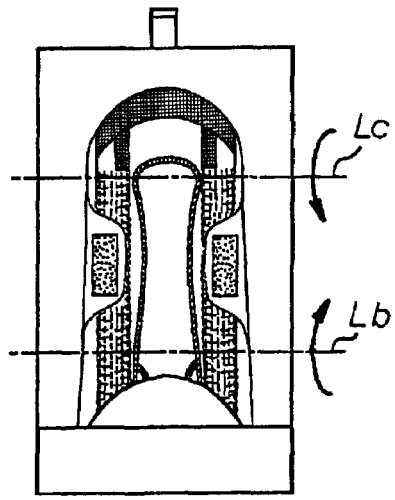
Figure 11C:
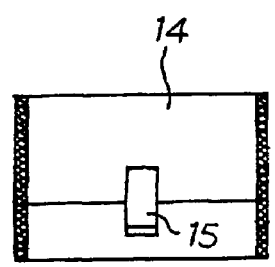

First, as shown in FIG. 11(*a*), the sanitary napkin 1" is placed on a packaging material 14. Also, a viscous portion 71 for fixing the wing portion 7 to the outer surface of an undergarment such as a shorts or the like is covered with a peelable sheet (not shown) and kept protected until the time for use of the napkin.

Then, the napkin 1" thus placed on the packaging material 14 is folded longitudinally along a fending line La extending in the widthwise direction (widthwise direction of the napkin) at a part near the rear end section D in the rear section B. Then, as shown in FIG. 11(*b*), the napkin 1" is longitudinally folded along a folding line Lb extending in the widthwise direction in the vicinity of the boundary between the excretion portion facing section A and the rear section B and further longitudinally folded along a folding line Lc extending in the widthwise direction in the vicinity of the boundary between the front end section C and the excretion portion facing section A.

Then the opposite side portions of the packaging material 14 extending widthwise outwards from the opposite side edges of the napkin 1" thus folded are sealed by the known method such as embossing processing or the like, and a tab tape 15 of the packaging material 14 is attached to a predetermined place. In this way, a packaging item of the sanitary napkin 1" shown in FIG. 11(*c*) can be obtained.

The leak preventive wall 5 in the napkin 1" of this embodiment is not raised at the part overlapped with the folding line La nearest to the rear end section D side, of all the folding lines La through Lc of the napkin which are formed for the purposes of obtaining an packaging item. That is, the leak preventive wall 5 at its part overlapped with the folding line La is prohibited from being raised (not raised) by being fixed, at least as the widthwise inner side (inward extension 52*a*) of the elastic expansible/contractible portion 52, to the topsheet 2.

By providing the end portion on the napkin rear end side of the part where the leak preventive wall 5 is raised, to a place not reaching the folding line La, the enhancement effect of fittability attributable to a provision of a part having a long distance from the upper end portion P of the basal wall portion 51 to the leak preventive layer (backsheet 3) and a low part, can surely be exhibited. That is, if the part where the leak preventive wall 5 is raised is overlapped with the folding line La, a large difference in height occurs between the upper surface (skin contact surface) of the leak preventive wall 5 and the upper surface (skin contact surface) of the absorbent layer E due to folding habit of the folded part by the folding line La. This possibly makes it impossible to fully exhibit the effect, which would otherwise be obtained by lowering the height of the leak preventive wall in the rear section B. However, by designing such that the part (50A and/or 50B) where the leak preventive wall 5 is not raised is not overlapped with the folding line La, such inconveniences can be avoided.

According to the napkin 1" of this embodiment, the same effect as in the above-mentioned sanitary napkin 1 can be obtained. Moreover, according to the above-mentioned manufacturing method of the sanitary napkin 1", the sanitary napkin 1" can be manufactured easily and economically.

It should be noted that the present invention is not limited to the above-mentioned embodiments and that many changes and modifications can be made without departing from the subject matter of the present invention.

Figure 12A:
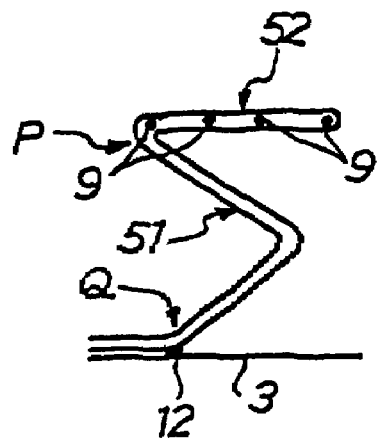
FIG. 12(a) and FIG. 12(b) are schematic views showing another form of a leak preventive wall.
Figure 12B:
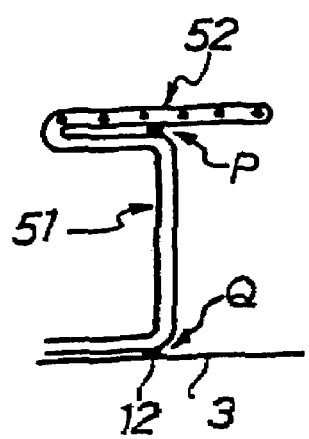

For example, in case of employment of the T-shaped leak preventive wall, the inward extension 52a and the outward extension 52b may be same or different in extension width. It is also accepted that the outward extension 52b is larger in extension width. Moreover, the leak preventive wall may have the sectional configuration as shown in FIG. 12(a) or 12(b). Reference numeral 12 of FIGS. 12(a) and 12(b) denotes an adhesive agent for joining the sheets together.

The multilayer portion 58 in the third embodiment may be formed by folding a part of the basal wall portion forming sheet portion 53 such that the surfaces of the sheet portion 53 facing widthwise outwards of the napkin are faced with each other and then, joining the mutually facing surfaces together.

In the napkin of the above-mentioned embodiments, although the leak preventive wall is formed using an elastic expansible/contractible member which is even in width of the basal wall portion forming sheet portion in the longitudinal direction, it is also accepted that the width of the material itself of the basal wall portion forming sheet portion in the rear section B is made shorter than the width of the material of the basal wall portion forming sheet portion in the excretion portion facing section A.

Moreover, the leak preventive wall may be designed such that by adjusting the widthwise fixed position of the basal wall portion forming sheet portion and by increasing the width of the multilayer portion and the joining width, or increasing the number of layers in the multilayer portion, the distance L2 is reduced, in the rear section B, towards the rear end section D.

In the napkin 1 of the first embodiment, as shown in FIG. 2(b), by fixing the elastic expansible/contractible member 50 onto the absorbent core in the rear section, the widthwise fixed position of the basal wall portion forming sheet portion in the excretion portion facing section A is differentiated from the widthwise fixed position of the basal wall portion forming sheet portion in the rear section B. It is also an interesting alternative that by fixing the elastic expansible/contractible member 50 in the rear section to the leak preventive layer (backsheet 2) F in the outer area of the absorbent layer F, the widthwise fixed position (see FIG. 2(a)) of the basal wall portion forming sheet portion in the excretion portion facing section A is differentiated from the widthwise fixed position of the basal wall portion forming sheet portion 53 in the rear section B, thereby making the distance L2 from the upper end portion P of the basal wall portion 51 to the leak preventive layer F in the rear section shorter than the distance L1 (see FIG. 2(a)) in the excretion portion facing section. In the example shown in FIG. 13, the multilayer portion 58 of the basal wall portion forming sheet portion is formed on the leak preventive layer, and a pocket is formed between the outer area of the absorbent layer and the basal wall portion 51 in the rear section. The napkin of this example can exhibit the effect of leak prevention significantly particularly in the case where a large quantity of excretion occurs.

Figure 13:
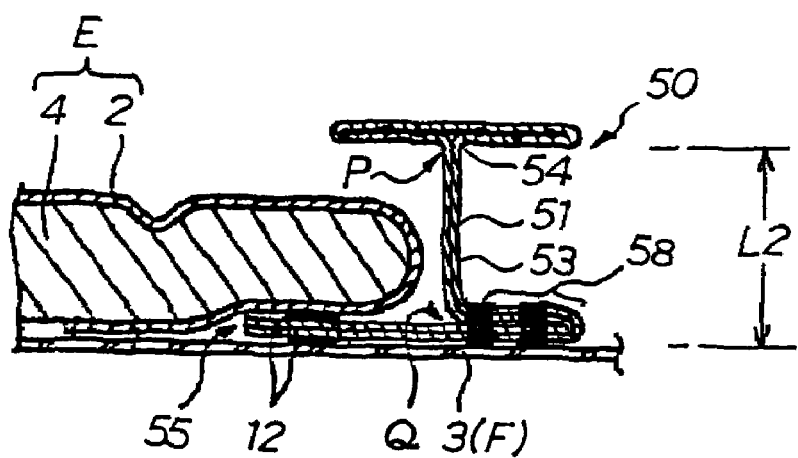
FIG. 13 is a sectional view showing an essential portion of a sanitary napkin according to another embodiment of the present invention.

As apparent from the foregoing, in both the first embodiment and the form shown in FIG. 13, in the rear section, the widthwise fixed position of the basal wall portion forming sheet portion is differentiated and the widthwise rising position of the leak preventive wall of the absorbent article is differentiated.

Moreover, in the napkin 1 of the first embodiment, although the leak preventive sheet 10 is disposed at the rear end section D in the longitudinal direction, such a leak preventive sheet can be disposed at the front end section C or at both the front end section C and the rear end section D.

The description omitted part in one embodiment and the important matters which only one embodiment has, can be applied, where appropriate, to other embodiments.

It should be noted that the absorbent article according to the present invention may be, besides a sanitary napkin, an incontinent pad, a panty liner, a disposable diaper or the like.

As fully described above, the absorbent article of the present invention is excellent in fittability and liquid leak preventive ability and hardly degraded in those excellent properties when in wear.

The invention being thus described, it will be obvious that the same may be is varied in many ways. Such variations are not to be regarded as a departure from the spirit and scope of the invention, and all such modifications as would be obvious to one skilled in the art are intended to be included within the scope of the following claims.

What is claimed is:

1. A sanitary napkin comprising a liquid retentive absorbent layer and a liquid impermeable leak preventive layer and including, in its longitudinal direction, an excretion portion facing section which is placed opposite a wearer's liquid excretion portion, when in wear, and a rear section,
    wherein a leak preventive wall is disposed on opposite side portions in the longitudinal direction, said leak preventive wall comprising a basal wall portion, a basal wall forming sheet portion, and a planar elastic expansible/contractible portion, wherein said planar elastic expansible/contractible portion is connected to an upper end portion of said basal wall portion by the basal wall forming sheet portion and wherein said elastic expansible/contractible portion is raised in said excretion portion facing section and in said rear section,
    wherein said elastic expansible/contractible portion in said excretion portion facing and rear sections comprises an inward extension which extends inwardly in the widthwise direction of said sanitary napkin from said upper end portion of said basal wall portion and an outward extension which extends outwardly in the widthwise direction of said sanitary napkin from said upper end portion such that in the portion where the leak preventive wall is raised in the excretion portion facing section and in the rear section, the leak preventive wall is in a shape of a T in section;
    wherein a skin contacting surface of said planar elastic expansible/contractible portion is generally parallel with a skin contacting surface of the said liquid retentive absorbent layer in the leak preventive wall of the excretion portion facing section;

wherein the widthwise inner side of said elastic expansible/contractible portion is not fixed to the top of said liquid retentive absorbent; and wherein the basal wall portion of the leak preventive wall of the rear section is multi-layered to form a multi-layered portion, said multi-layered portion is formed by folding a portion of the basal wall forming sheet into multiple layers and maintaining the folded state by joining the layered sheets with each other;

wherein a distance from an upper end portion of said basal wall portion to said leak preventive layer in said rear section having said multi-layered portion is shorter than a comparable distance in said excretion portion facing section;

wherein the basal wall portion, in the rear section, comprises a lower end portion, opposite to the upper end portion, which is sandwiched between the liquid retentive absorbent layer and the liquid impermeable leak preventive layer and wherein said lower end portion of said basal wall portion is adhered to both a lower surface side of the liquid retentive absorbent layer and an upper surface side of the liquid impermeable leak preventive layer;

wherein the basal wall portion, in the excretion portion facing section, comprises a lower end portion, opposite to the upper end portion, which is sandwiched between the liquid retentive absorbent layer and the liquid impermeable leak preventive layer and wherein said lower end portion of said basal wall portion is adhered to both a lower surface side of the liquid retentive absorbent layer and an upper surface side of the liquid impermeable leak preventive layer; and wherein the leak preventive wall forms a pocket located only above the top surface of the absorbent layer.

2. The sanitary napkin according to claim 1, wherein the multi-layered portion is not fixed to the inward extension.

3. The sanitary napkin according to claim 1, wherein each of said inward and outward extensions of said planar elastic expansible/contractible portion comprises three elastic members.

4. The sanitary napkin according to claim 1, wherein the distance from the distal end of the inward extension to the distal end of the outward extension of said planar elastic expansible/contractible portion is 10 to 30 mm.

5. The sanitary napkin according to claim 1, wherein each of said inward and outward extensions of said planar elastic expansible/contractible portion is generally the same when extended in the widthwise direction.

* * * * *

UNITED STATES PATENT AND TRADEMARK OFFICE
CERTIFICATE OF CORRECTION

| | | |
|---|---|---|
| PATENT NO. | : 7,641,642 B2 | Page 1 of 1 |
| APPLICATION NO. | : 10/322667 | |
| DATED | : January 5, 2010 | |
| INVENTOR(S) | : Murai et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 327 days.

Signed and Sealed this

Twenty-first Day of December, 2010

David J. Kappos
*Director of the United States Patent and Trademark Office*